(12) United States Patent
Harrop

(10) Patent No.: US 6,598,796 B2
(45) Date of Patent: Jul. 29, 2003

(54) METHOD AND APPARATUS FOR ALIGNING LABELS APPLIED TO A SPECIMEN COLLECTION CONTAINER

(75) Inventor: Andrew John Harrop, Okehampton (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/033,804

(22) Filed: Jan. 3, 2002

(65) Prior Publication Data

US 2002/0100806 A1 Aug. 1, 2002

Related U.S. Application Data

(60) Provisional application No. 60/260,790, filed on Jan. 10, 2001.

(51) Int. Cl.[7] .................................................. G06K 7/10
(52) U.S. Cl. ........................... 235/462.01; 235/462.13; 235/375; 235/385; 235/470; 422/941; 356/246
(58) Field of Search ........................ 235/462.01, 462.13, 235/470, 385, 375; 422/941, 945, 913, 914, 915, 916, 917, 918; 356/246

(56) References Cited

U.S. PATENT DOCUMENTS

| | | | |
|---|---|---|---|
| 3,680,967 A | | 8/1972 | Engelhardt |
| 4,753,358 A | * | 6/1988 | Virca et al. ................. 215/230 |
| 4,805,772 A | * | 2/1989 | Shaw et al. ................. 206/443 |
| 4,944,924 A | * | 7/1990 | Mawhirt et al. ............. 422/104 |
| 5,286,959 A | * | 2/1994 | Demachi ................ 235/462.14 |
| 5,646,389 A | * | 7/1997 | Bravman et al. ............ 235/385 |
| 5,663,545 A | * | 9/1997 | Marquiss ..................... 235/375 |
| 5,777,303 A | * | 7/1998 | Berney ........................ 235/375 |
| 5,985,215 A | * | 11/1999 | Sakazume et al. ............ 422/67 |
| 6,081,326 A | * | 6/2000 | Rousseau et al. ........... 356/246 |
| 6,141,602 A | * | 10/2000 | Igarashi et al. ............. 700/226 |
| 6,156,575 A | | 12/2000 | Fassbind et al. |
| 6,161,759 A | * | 12/2000 | Moss et al. ............ 235/462.01 |

FOREIGN PATENT DOCUMENTS

GB        1423 185        1/1976

* cited by examiner

Primary Examiner—Karl D. Frech
Assistant Examiner—Daniel I Walsh
(74) Attorney, Agent, or Firm—Nanette S. Thomas, Esq.; Scott J. Rittman, Esq.

(57) ABSTRACT

A method and apparatus provides for the establishment of position of readable information applied to a specimen collection container. Preferably, the readable information is provided by way of a scannable bar code label applied to the container. The label may be adhesively applied to the container, and includes a non-adhesive portion which results in that portion of the label protruding from the container. The container is then supported within a container holder. The holder itself has a projection which becomes engaged with the protruding portion of the label. The container holder is agitated to effect movement of the container to place the protruding portion of the label into engagement with the projection, and thereby prevent further movement of the container and establish the position of the readable information contained on the label.

11 Claims, 4 Drawing Sheets

METHOD AND APPARATUS FOR ALIGNING LABELS APPLIED TO A SPECIMEN COLLECTION CONTAINER

This application claims the benefit of Provisional Application No. 60/260,790, filed Jan. 10, 2001.

BACKGROUND OF THE INVENTION

1. Field of Invention

The present invention relates generally to specimen collection containers and more particularly relates to a method and apparatus for aligning readable information applied to a plurality of specimen collection containers.

2. Description of Related Art

It is common for medical specimens to be collected by a technician in a collection container for subsequent testing. Blood specimens are typically collected in blood collection tubes. These tubes are transported or shipped to a test facility together with documentation relating to the particular test and to the patient from which the blood specimen was taken.

Much of the information which identifies the test, and/or the patient, can be reduced to a scannable bar code which can be placed on the blood collection tube. The bar code is typically applied to the tube by use of an adhesive label where it can be conveniently scanned by a bar code scanner to provide the requisite information to the medical technician. Bar code scanning is often done with a hand-held scanner, or alternatively, with a fixed bar code reader.

In either case, it is necessary to properly orient the blood collection tube so that the scannable bar code is conveniently presented to the bar code reader. Quite often, orientation requires manual rotation of the tube to assure that the scannable bar code can be read by the scanner. In other situations, pick and place mechanisms may be used to lift and rotate the tube to provide such orientation. As may be appreciated, individual manual rotation of a plurality of tubes is difficult, time-consuming and subject to manual error. Mechanical devices which lift and rotate the tube are cumbersome to use and costly.

Another prior art solution to the alignment of bar codes is to apply the bar code continuously around the circumference of the tube. This allows the bar code to be read regardless of the rotational orientation of the tube. However, employing a bar code label of this type has several disadvantages. First, due to the increased size of the bar code, there is little additional space for the user to apply requisite information at the blood collection site. Additionally, continuous bar code labels of this type are expensive to manufacture and difficult to apply.

There exists a need to improve the efficiency and accuracy of aligning scannable bar codes on a plurality of labeled specimen collection containers.

SUMMARY OF THE INVENTION

The present invention provides a method and apparatus for establishing the position of readable information applied to a specimen collection container.

Preferably, the readable information is provided by way of a scannable bar code label applied to the container.

More preferably, the label includes a non-adhesive section which results in a portion of the label protruding from the container. The container is then movably supported within a container holder. The holder itself has a projection engageable with the protruding portion of the label upon movement of the container therein. The container holder may be agitated to effect movement of the container to place the protruding portion of the label into engagement with the projection, and thereby prevent further movement of the container and establish the position of the readable information contained on the label.

Preferably, the present invention includes a container rack having a plurality of cavities for individually accommodating a plurality of specimen collection containers. The rack includes a projecting stop which is engageable with the protrusion on the label. The rack may be vibrated to cause rotative movement of the containers in the cavities to place label protrusions in engagement with the projections which serves as a stop to align the scannable portions of the labels.

DETAILED DESCRIPTION

Figure 1:
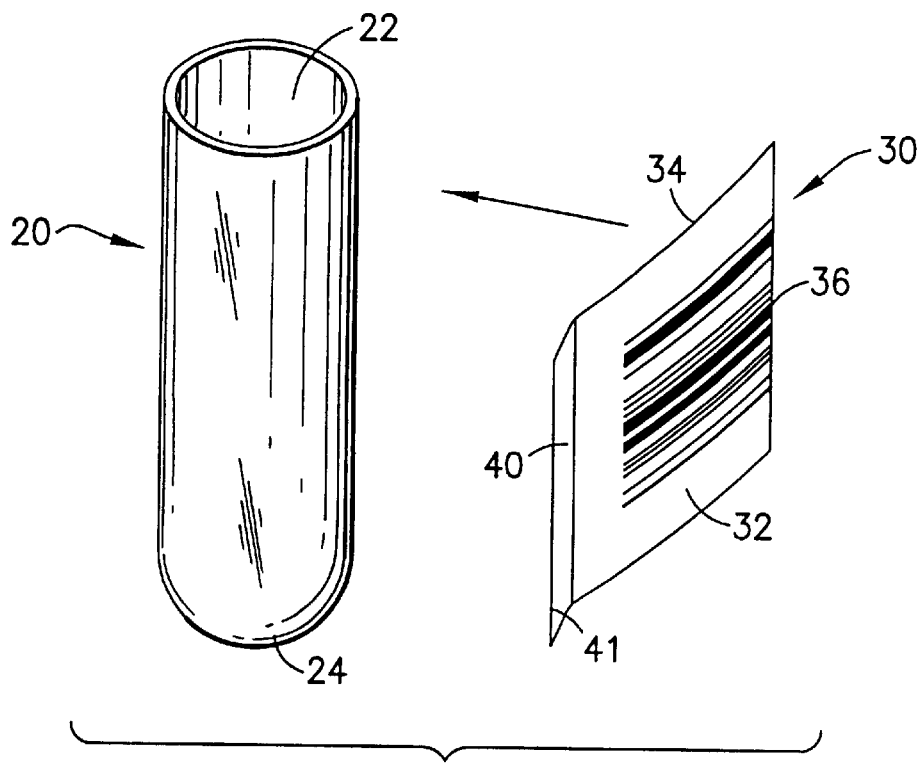
FIG. 1 is a perspective showing of a specimen collection container, including a bar code label which is applied thereto, for use in accordance with the present invention.

While this invention is satisfied by embodiments of many different forms, there is shown in the drawings, and will be described in detail hereinbelow, the preferred embodiments in the invention with the understanding that the present disclosures will be considered as exemplary of the principles of the invention, and is not intended to limit the invention to the embodiments illustrated. Various other modifications will be apparent to and readily made by those skilled in the art without departing from the scope and spirit of the invention. The scope will be measured by the appended claims and their equivalents.

Figure 2:
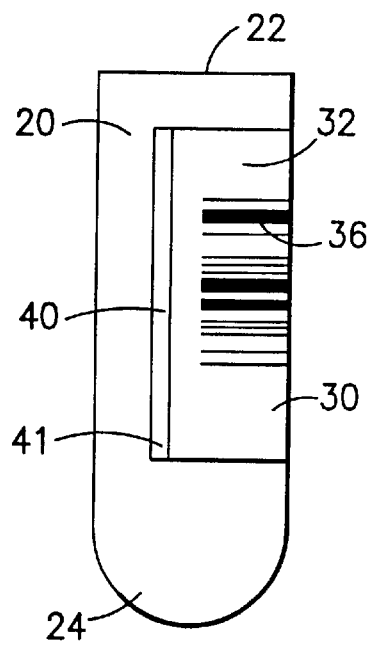
FIG. 2 is a front plan view of the specimen collection container of FIG. 1, with the bar code label applied thereto.
Figure 3:
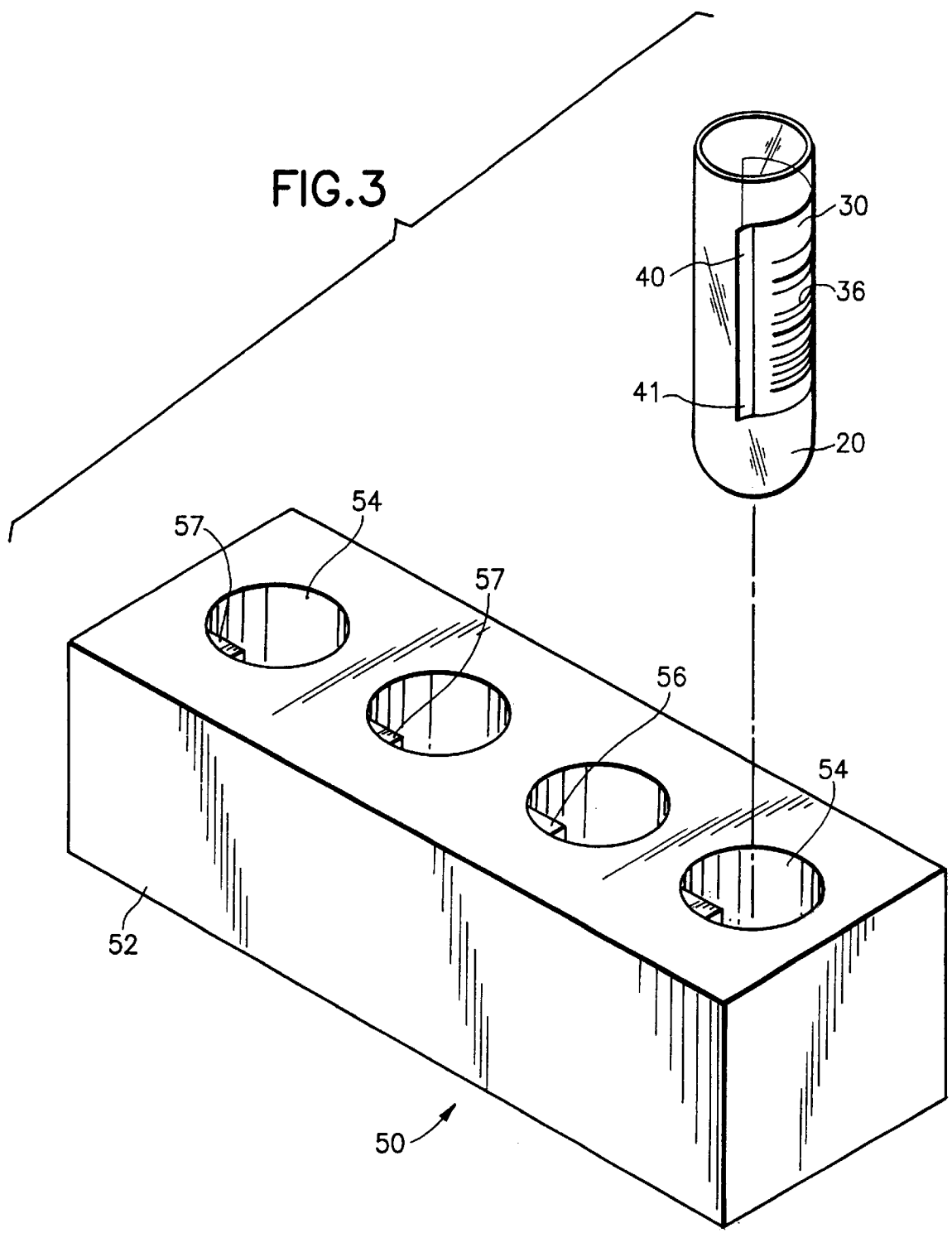
FIG. 3 is a perspective showing of a specimen collection tube of FIG. 2, insertable into a container rack.

Referring to FIGS. 1 and 2, a sample collection tube 20 and an associated label 30 are shown. Tube 20 is an elongate, generally cylindrical member having an open upper end 22 and a closed lower end 24. The open upper end 22 may be closed by a removable stopper.

In order to identify the sample contained in a particular blood collection tube, label 30 may be applied thereto. The labels which are used in combination with blood collection tubes may include various identifying indicia and, as particularly shown in the present invention, may include a scannable bar code. The information contained in the scannable bar code may assist in providing information regarding the patient, the particular sample taken, tests to be performed or tests which have been performed on the sample contained in the container.

Label 30 is generally a planar member having first surface 32 and opposed second surface 34. First surface 32 may include the identifying indicia such as the scannable bar code 36 arranged at a preselected location thereon. Opposed second surface 34 is typically applied to the tube 20 to affix label 30 to the tube. Second surface 34 may include an adhesive coating so as to adhesively adhere label 30 to tube 20.

Figure 4:
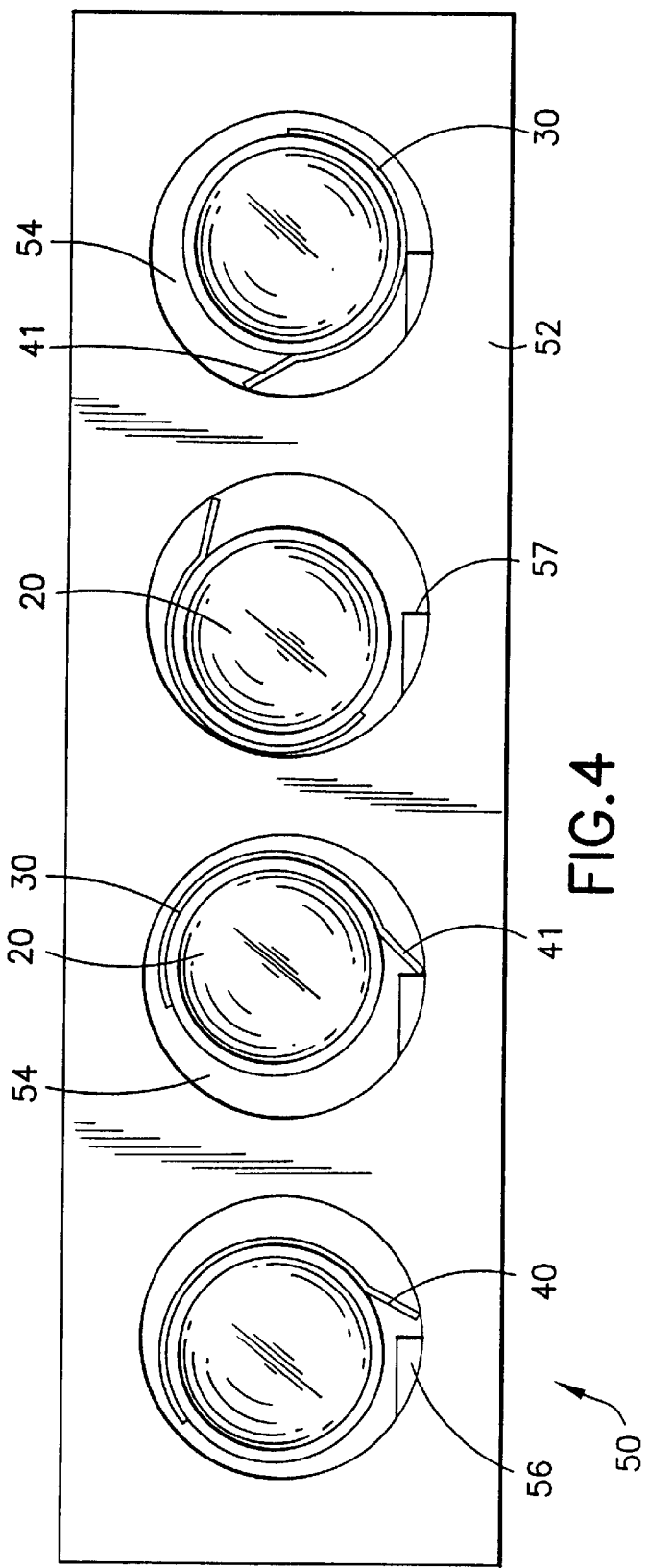
FIG. 4 is a top view of a plurality of specimen collection containers of FIG. 2, shown supported within cavities of the container rack of FIG. 3.

Label 30 further includes an extending edge portion 40. Edge portion 40 is an elongate member extending along one longitudinal side of label 30. Edge portion 40 is defined by a fold line 42 which joins edge portion 40 to the remainder of label 30. Unlike label 30, edge portion 40 includes no adhesive coating on either side thereof. Thus, as shown in FIG. 2, upon application of label 30 to tube 20, edge portion 40 remains unadhered to tube 20. The non-adhesion of edge portion 40 to tube 20 causes the edge portion to protrude readily outward from the surface of tube 20. Thus, the non-adhered edge portion 40 forms a protruding tang 41 as viewed from above as shown in FIG. 4. Protruding tang 41 formed by edge portion 40 may be used to provide for mutual alignment of the bar codes 36 contained on labels 30 on a plurality of tubes 20.

One or more tubes 20, having labels 30 placed thereon, may be supported in a container holder or rack 50. Rack 50 may be of conventional construction, including an elongate body 52 having a plurality of longitudinally spaced, open ended cavities 54 which loosely accommodate one of a plurality of tubes 20.

Rack 50 is constructed so that body 52 includes a projection 56 extending into each cavity 54. Projection 56 may be formed in the sidewall of cavity 54 to project a short distance inwardly toward the center of the cavity. The distance of extension of projection 56 is sufficiently small to allow rotative movement of tube 20 within cavity 54, yet of sufficient distance to place the extending tang 41 formed by edge portion 40 in engagement therewith upon such rotation. Each projection 56 in cavity 54 is mutually aligned with respect to body 52 of rack 50. Thus, as particularly shown in FIG. 4, each projection 56 defines stop surface 57, which is similarly positioned in each cavity 54. In the embodiment shown in FIG. 4, each stop surface 57 may be identically positioned at, for example, the "6 o'clock" position as viewed from above.

Figure 5:
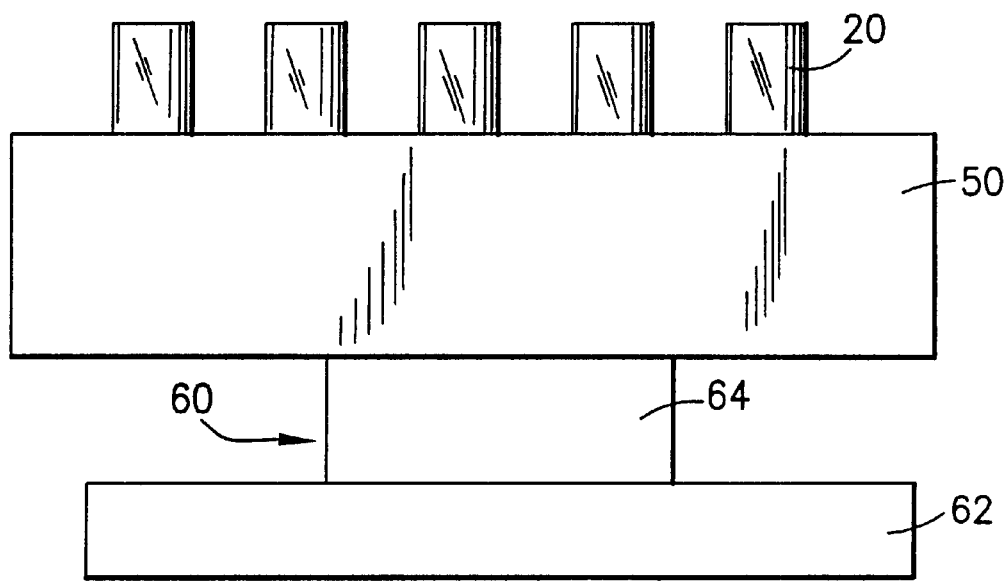
FIG. 5 is a front plan view of the container rack, including the supported containers positioned on vibrating pedestals.
Figure 6:
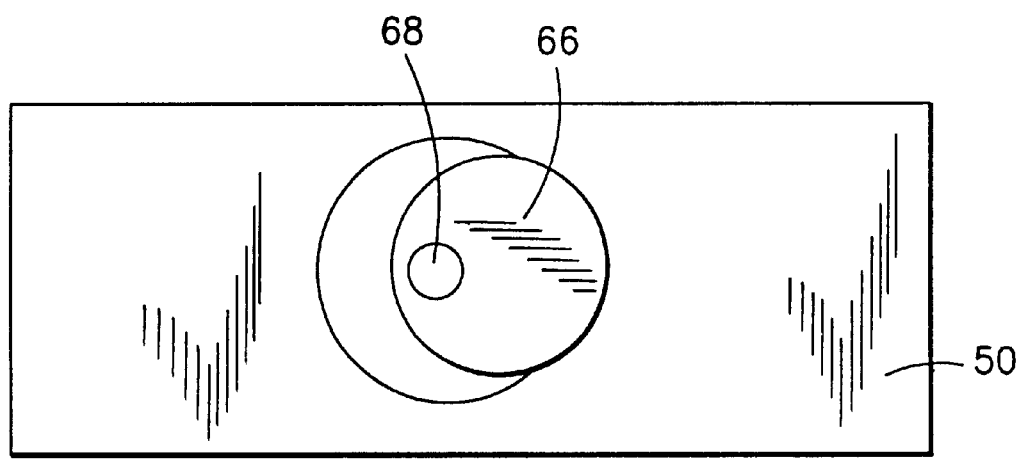
FIG. 6 shows an example of a mechanism, including the pedestal of FIG. 5, for effecting vibratory/rotary motion of the container holder.

Referring now to schematic FIGS. 5 and 6, rack 50 including a plurality of tubes 20 supported therein, may be supported by a vibrating mechanism 60. Vibrating mechanism 60 is designed to agitate rack 50 so as to impart motion to the tubes held therein and may be any of a wide variety of mechanisms which affect vibratory motion. Vibrating mechanism 60 may include a base 62, and an upwardly extending central portion 64 which directly supports rack 50. As more particularly shown in FIG. 6, one vibrating mechanism may include rack 50 forming an off-centered mass about a central eccentric shaft 66. Shaft 66 is rotatable about a central rod 68 to effect movement of base 62 therearound. Vibratory mechanism 60 is designed so as to effect movement to rack 50 which imparts rotational movement to tubes 20 contained in cavities 54 of body 52.

As shown in FIG. 4, vibratory movement of mechanism 60 causes rotational movement of tubes 20, preferably a clock-wise direction, within cavities 54. The tubes then rotate until the protruding tang 41 of edge portion 40 engages stop surface 57 of projection 56 thus stopping the rotational movement of tube 20. By positioning projection 56 at aligned positions with respect to body 52, each tube 20 will be stopped at the identical position with respect to the position of label 30 on tube 20. In this manner, a hand-held or automatic scanner can now quickly and accurately scan the bar coded information contained on label 30 as the bar coded information on the label will be presented in the same orientation with respect to each tube. It may be appreciated that projection 56 may be placed at any desired position within cavity 54 so as to place the bar coded information at any desirable mutually aligned position with respect to rack 50.

What is claimed is:

1. A method for positioning a container in a holder so that information on the container is readable, comprising the steps of:

a) adhering a label having readable information thereon to a container, a portion of said label protruding from said container;

b) movably supporting said container with a container holder, said holder -having a projection engageable with said protruding portion of said label; and c) agitating said container holder to effect movement of said container so that said protruding portion engages said projection with said container stopped in a position whereby said information is readable.

2. The method of claim 1 wherein said adhering step is performed with an adhesive, said adhesive being excluded from said protruding portion.

3. The method of claim 1 wherein said label is a bar code label and said readable information includes a scannable bar code.

4. The method of claim 1 wherein said container holder includes a container rack having a cavity for movably accommodating said container therein, said rack further including said projection extending into said cavity defining a stop for engagement with said protruding portion of said label.

5. The method of claim 4 wherein said agitating step is performed by vibrating said rack to cause rotative movement of said container in said cavity.

6. The method of claim 4 wherein said rack is elongate and includes a plurality of said cavities for accomodating a plurality of said containers, each cavity having one said projection extending thereinto, said projections being in mutual alignment.

7. The method of claim 6 wherein said agitating step includes:

vibrating said rack to cause rotative movement of said container in said cavities to place each said protruding portion of said label in engagement with said stop defined by said projection so as to mutually align said readable information on said labels.

8. A specimen collection container alignment system comprising:

a plurality of specimen collection containers;

a bar code label applied to each said container, each said label having a scannable bar code and a protruding portion extending from said container;

a container rack having a plurality of cavities for accommodating said containers, each cavity having a projection extending thereinto; and means for agitating said rack to cause movement of said containers in said cavity to place said protruding portions in engagement with said projections to stop said movement thereof and align said scannable bar codes on said labels.

9. The specimen collection container alignment system of claim 8 wherein said agitating means includes means for vibrating said rack.

10. The specimen collection container of claim 8 wherein said label is an adhesive label and wherein said protruding portion is defined by an extent of said label having no adhesive thereon.

11. The specimen collection container of claim 9 wherein said vibrating means includes:

an electric motor having a rotating shaft; and a rack support fixed to said shaft to support said rack offset from the shaft center.

* * * * *